(12) United States Patent
Raz

(10) Patent No.: US 6,372,447 B1
(45) Date of Patent: Apr. 16, 2002

(54) METHOD OF DISTRIBUTING CELLS AS SINGLE LAYER ON A SUBSTRATE FROM A SUSPENSION

(75) Inventor: Ryan S. Raz, Toronto (CA)

(73) Assignee: Veracel Inc., Toronto (CA)

( * ) Notice: Subject to any disclaimer, the term of this patent is extended or adjusted under 35 U.S.C. 154(b) by 0 days.

(21) Appl. No.: 09/389,217

(22) Filed: Sep. 3, 1999

Related U.S. Application Data

(63) Continuation of application No. PCT/CA98/00501, filed on May 21, 1998.
(60) Provisional application No. 60/047,482, filed on May 23, 1997.

(51) Int. Cl.[7] .......................... C12Q 1/24; C12N 11/16; C12N 1/02; C12N 5/00; C12M 2/26
(52) U.S. Cl. .................. 435/30; 435/174; 435/177; 435/261; 435/395; 435/287.1; 435/308.1; 435/309.1
(58) Field of Search .................. 435/30, 174, 177, 435/234, 325, 261, 395, 287.1, 308.1, 309.1

(56) References Cited

U.S. PATENT DOCUMENTS

| | | | |
|---|---|---|---|
| 5,591,627 A | 1/1997 | Miyamoto | 435/240.23 |
| 5,602,042 A | 2/1997 | Farber | 436/526 |
| 6,291,234 B1 * | 9/2001 | Raz et al. | 435/309.1 |

FOREIGN PATENT DOCUMENTS

| | | |
|---|---|---|
| EP | 0 120 187 A1 | 10/1984 |
| EP | 0 589 293 A2 | 3/1994 |
| EP | 0 590 506 A1 | 4/1994 |

* cited by examiner

*Primary Examiner*—David M. Naff
(74) *Attorney, Agent, or Firm*—Ridout & Maybee LLP; William B. Vass

(57) ABSTRACT

An apparatus and method are provided for preparing specimens of biological cells uniformly distributed over a substrate surface. The method comprises providing a suspension of biological cells in fluid, and then extracting biological target cells from the suspension to leave debris and contaminants behind. The extracted target cells are distributed over a substrate surface into a primary layer of cells coupled to the substrate surface with the remaining cells forming a secondary layer on top of the primary layer. The target cells forming the secondary layer are then removed to produce a substantially non-overlapping layer of target cells coupled to the substrate surface.

15 Claims, 16 Drawing Sheets

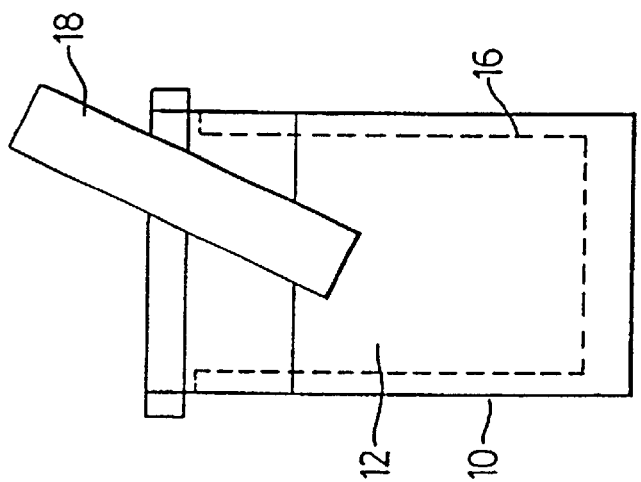
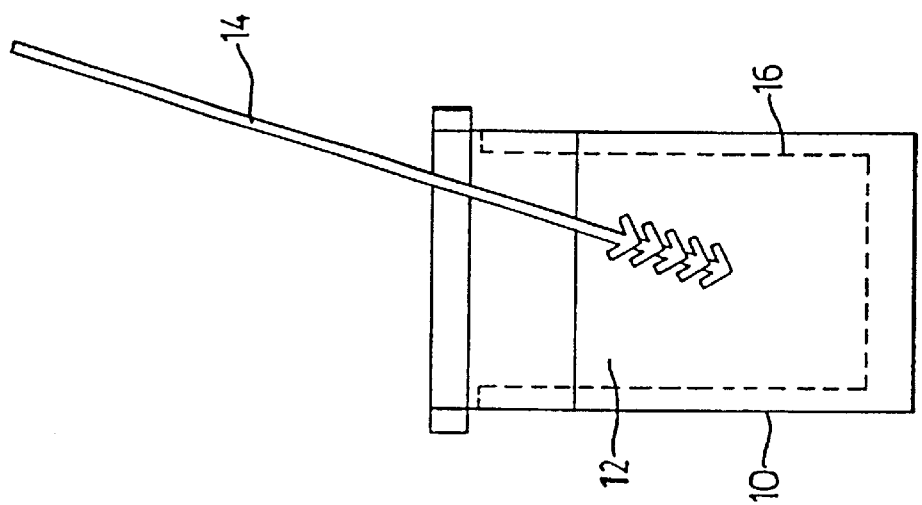

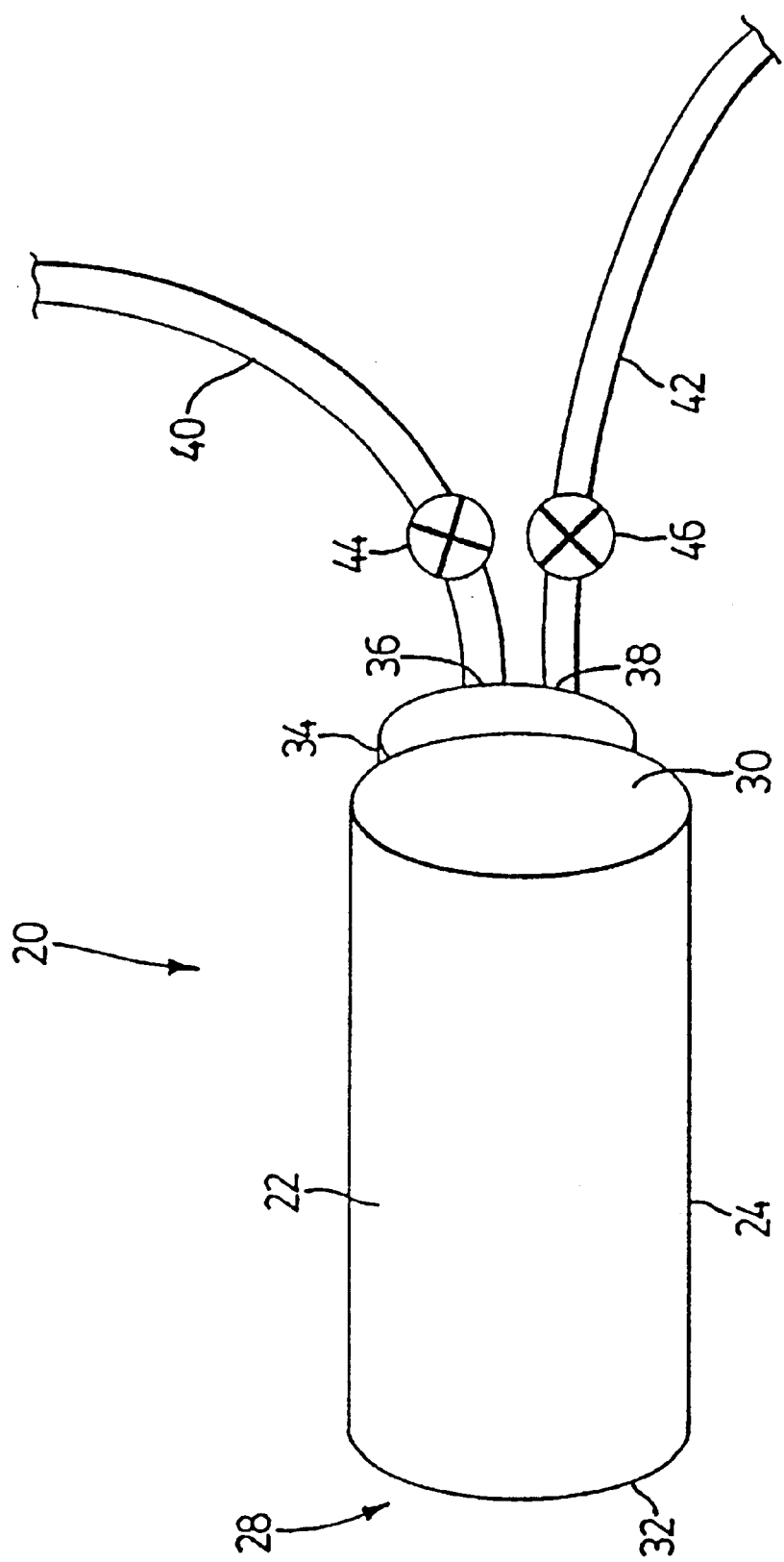

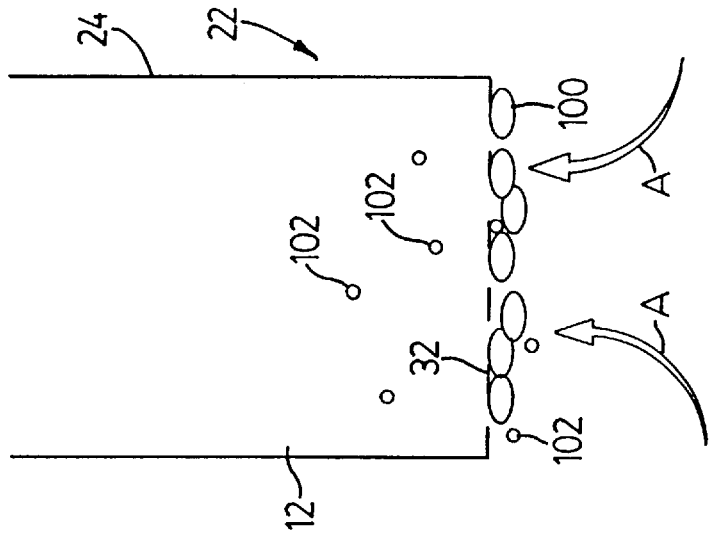
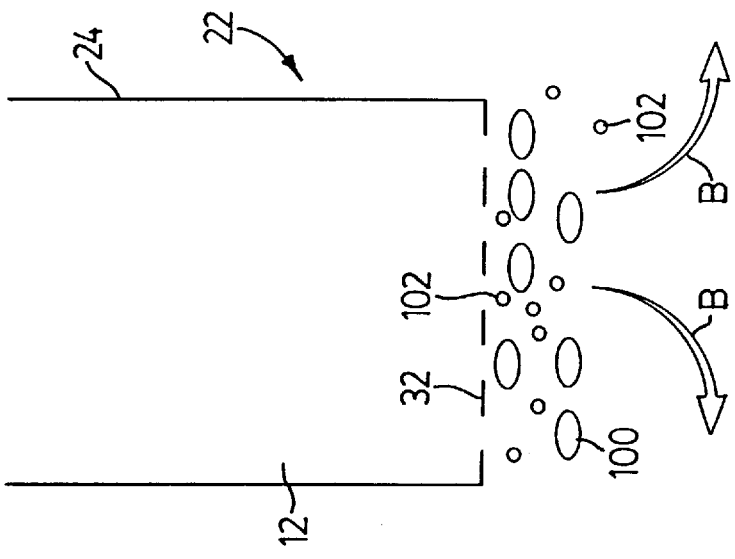
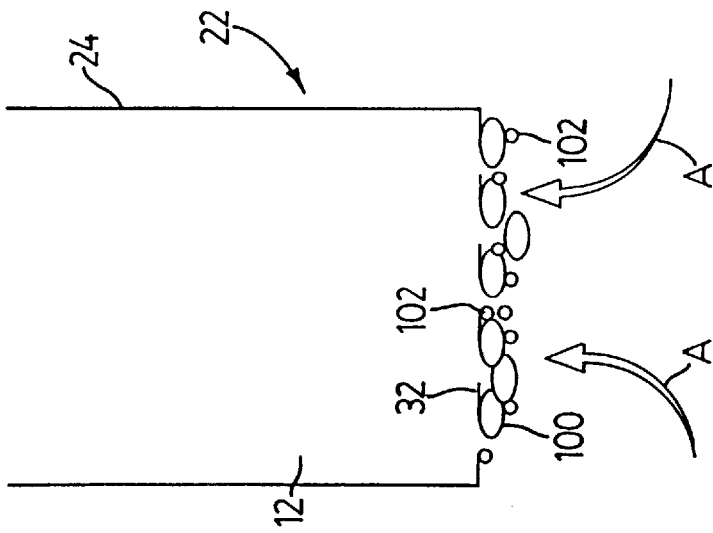
FIG. 5c
FIG. 5b
FIG. 5a

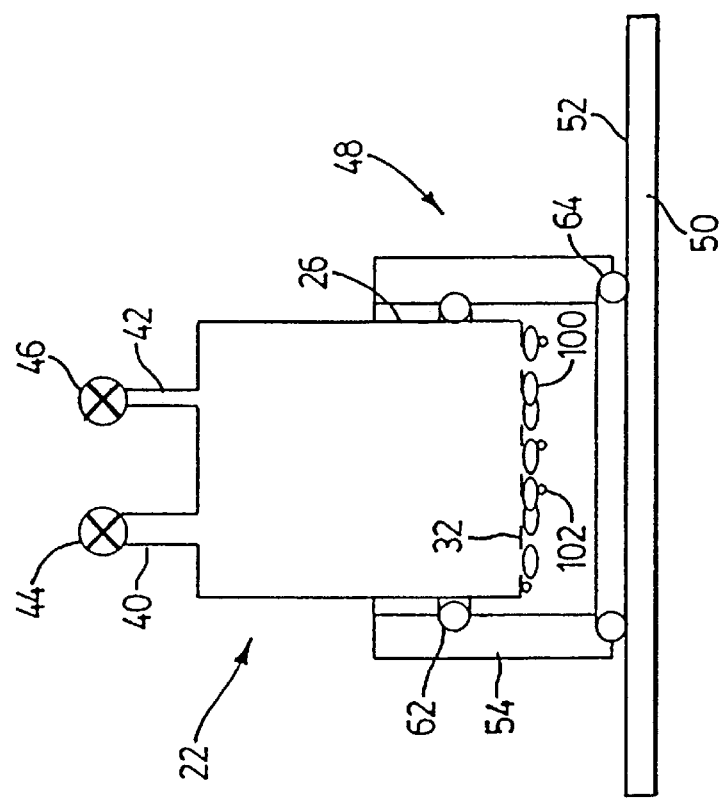
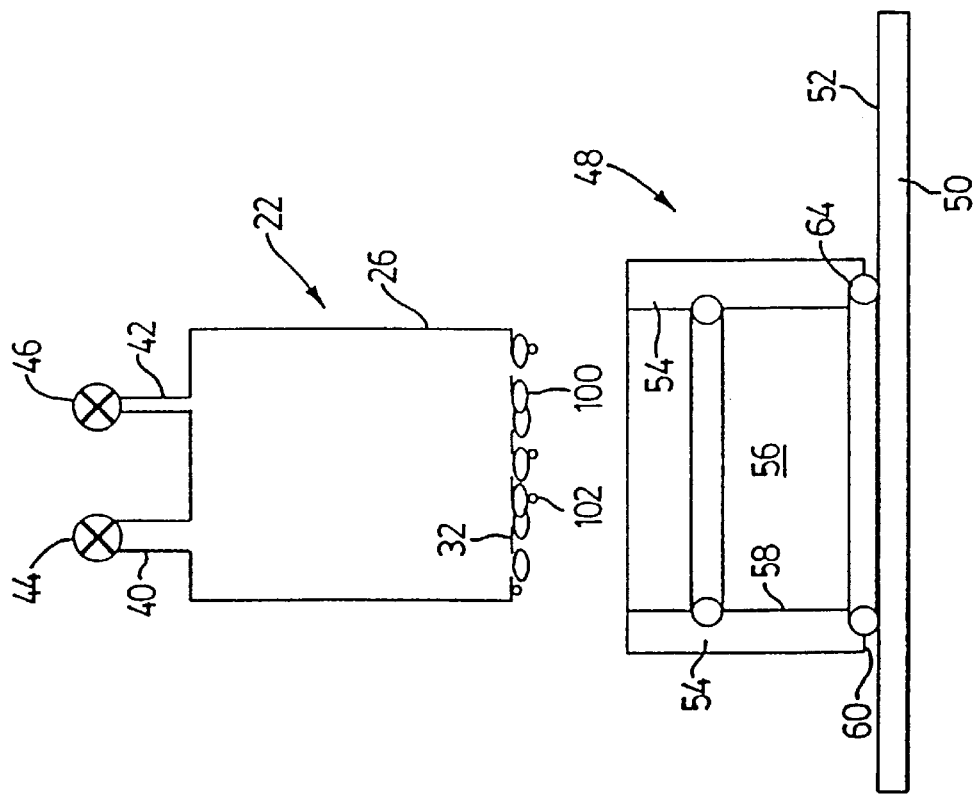
FIG. 7a
FIG. 7b

METHOD OF DISTRIBUTING CELLS AS SINGLE LAYER ON A SUBSTRATE FROM A SUSPENSION This application is a continuation of our co-pending International Patent Application No. PCT/CA98/00501 filed May 21, 1998, and claims benefit under 35 U.S.C. § 119(e) of U.S. Provisional Application No. 60/047,482, filed May 23, 1997.

FIELD OF THE INVENTION

The present invention relates to a method for preparing a specimen from a cellular suspension of biological cells. In particular, the invention relates to a method for preparing a specimen comprising a uniform distribution of biological cells on a substrate surface.

BACKGROUND OF THE INVENTION

The collection or preservation of biological cells in fluid suspension is common in medicine and biology for the detection of disease. For example, naturally voided urine contains urothelial cells from the lining of the bladder. If the urothelial cells are separated from the urine and then placed on a substrate surface, such as a microscope slide, examination of the cells can determine the presence or absence of certain diseases. Another example is the PAP Smear Test which involves the artificial exfoliation of epithelial cells from the cervix of the uterus and the subsequent suspension of the exfoliated epithelial cells in a water/alcohol solution to preserve and protect the cells. If the epithelial cells are separated from the solution and then deposited on a microscope slide, examination of the cells can determine the presence or absence of precancerous lesions on the cervix.

However, current techniques for the preparation of specimens from cellular suspensions are deficient since the cellular suspensions may contain debris and contaminants which can interfere with the examination of the desired ("target") cells. For instance, in the case of cervical epithelial specimens, the contaminants may include leukocytes, erythrocytes, bacteria and mucus. In addition, the typical specimen may contain several layers of cells and/or the cells may overlap one another, thereby rendering the detection of cell abnormalities difficult. Another reason is that, for the Pap test or indeed any other type of test requiring an exfoliation instrument, the technique of transferring the collected cells from the exfoliation instrument to the glass slide can be very inefficient. In some studies it has been shown that less than 20% of the collected sample is effectively transferred. By contrast, a liquid-based specimen allows, as a preliminary step, all of the collected cells to be rinsed or washed off of the exfoliation instrument into the collection fluid thereby improving specimen recovery and aiding in subsequent diagnostic accuracy.

Accordingly, there is a need for a method for preparing specimens from cellular suspensions which enhances the ease and accuracy of evaluation of biological cells for abnormalities.

SUMMARY OF THE INVENTION

According to the present invention, there is provided a method and apparatus for preparing specimens from cellular suspensions which enhances the specimen recovery as well as the ease and accuracy of evaluation of biological target cells for abnormalities.

The method comprises the steps of providing a suspension of biological cells in fluid wherein said cells include biological target cells; extracting a portion of the biological target cells from the suspension; distributing the extracted portion over a substrate surface into a primary layer with the remaining extracted biological target cells being located on top of said primary layer; and removing the plurality of cells located on top of the primary layer.

Specimens prepared according to the above method are substantially free of debris and contaminants. In addition, the cells comprising such specimens are densely packed into a single layer with little cell overlap. Therefore, the ease and accuracy of detection of cell abnormalities is greatly enhanced.

In another aspect, the present invention provides an apparatus for preparing a biological cellular specimen on the surface of a substrate, said apparatus comprising: a filter tube including an outlet port and a porous filter medium coupled to the outlet port; a tubular member having an interior region and a pair of opposite ends, and including means for receiving said filter tube within said interior region; and means for sealingly coupling the surface of said substrate to one of the ends of said tubular member.

BRIEF DESCRIPTION OF THE DRAWINGS

Reference will now be made to the accompanying drawings, which show by way of example, a preferred embodiment of the present invention, and in which:

FIGS. 1(a) and 1(b) are schematic views of an apparatus for performing the cellular suspension method according to the present invention;

FIG. 2 is a schematic view of a filter tube for performing the extraction step and the distribution step;

FIGS. 5(a) to 5(c) are magnified schematic views of the filter tube during a back-flushing stage of the extraction step, showing the biological target cells in suspension and the membrane filter;

FIGS. 7(a) to 7(b) are magnified schematic views of one variation of the filter tube and substrate;

DETAILED DESCRIPTION OF THE PREFERRED EMBODIMENT

Figure 3:
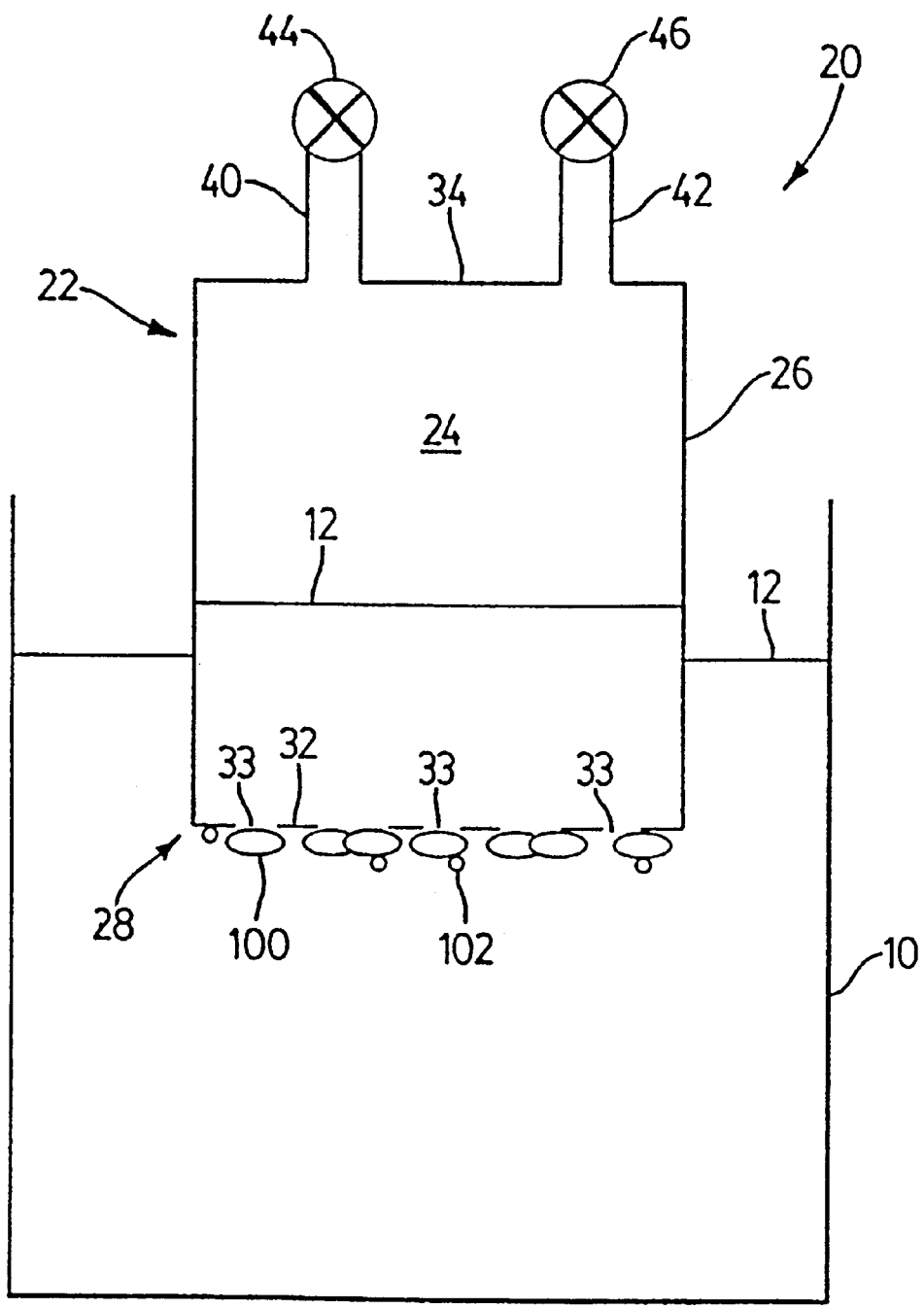
FIG. 3 is a schematic view of the filter tube shown in FIG. 2, immersed in a cellular suspension.

Reference is first made to FIG. 1(a) which shows a collection vessel 10 for providing a suspension of biological cells in accordance with the present invention. The collection vessel 10 is filled with a preservation fluid or medium 12. The preservation medium 12 comprises water and alcohol, or other known anti-microbial compounds. Biological cells for the cellular suspension are introduced into the collection vessel 10 using a cell collection implement 14. The cell collection implement 14 contains biological cells obtained through an artificial cellular exfoliation procedure, and is inserted into the preservation fluid 12 in the collection vessel 10. For example, the collection implement 14 may contain uterine cervical epithelial cells obtained through a PAP Smear. The exfoliated cells are rinsed from the collection implement 14 into the preservation fluid 12, which preserves the cells until a specimen is prepared as will be discussed below.

As shown in FIG. 1(a), the collection vessel 10 includes a catch basket 16 to allow the technician to easily remove the collection implement 14 from the vessel 10.

In one variation, as shown in FIG. 1(b), the collection implement 14 is replaced with a cell collection vial 18. The collection vial 18 contains naturally exfoliated cells which are obtained through a natural exfoliation process. For example, the collection vial 18 may include urothelial cells filtered from naturally voided urine. The collection vial 18 is inserted into the collection vessel 10, and the exfoliated cells in the collection vial 18 are rinsed into the preservation fluid 12. The preservation fluid 12 preserves the exfoliated cells until a specimen can be prepared.

After rinsing the exfoliated cells into the preservation fluid 12 in the collection vessel 10, the next step involves disaggregating the cells in order to place the cells in suspension in the preservation fluid 12. During the disaggregation step, the collection vessel 10 undergoes vortex motion in which the collection vessel 10 is repeatedly rotationally accelerated and decelerated about the longitudinal axis of the collection vessel 10 to break apart any randomly-bonded cellular groups or cell clusters. The disaggregation step continues until a desired level of cellular suspension has been obtained.

After the disaggregation step, a filter tube 20 as shown in FIG. 2 is used to extract the desired ("target") biological cells from the suspension of cells. The filter tube 20 comprises a tubular member 22 having an exterior outer surface 24 (which defines an interior cylindrical volume 26) and a pair of open opposite ends 28, 30. A disc-shaped membrane filter 32 seals one end 28 of the tubular member 22. As shown in FIG. 2, the membrane filter 32 includes a plurality of pores. The pores are larger that the debris, mucus and contaminants which may be present in the preservation fluid 12 but smaller than the biological target cells so that the debris, mucus and contaminants are allowed to pass through the membrane filter 32, while the biological target cells are not.

The other end 30 of the tubular member 22 includes a disc-shaped lid 34 which seals the end of the member 22. The lid 34 includes outlet ports 36, 38 which communicate with the interior of the tubular member 22. The outlet port 36 is coupled to a suction tube 40 through a valve 44. Similarly, the other outlet port 38 is coupled to a drain/fill tube 42 through another valve 46. The valves 44, 46 allow the respective tubes 40, 42 to be selectively opened and closed.

Figure 4:
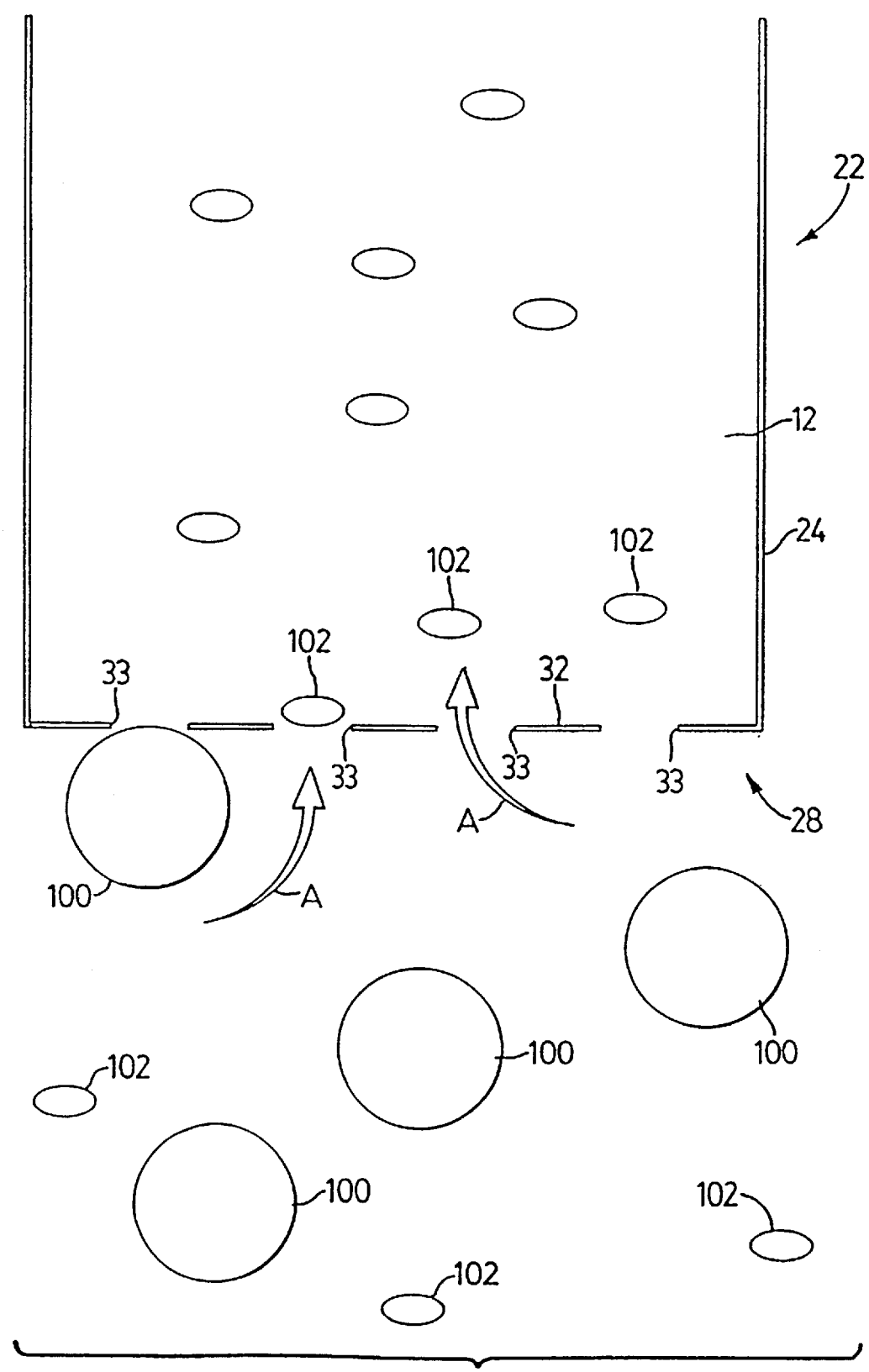
FIG. 4 is a magnified schematic view of the filter tube during the extraction step, showing the biological target cells and the debris in suspension, and the membrane filter.

During the disaggregation step, the tubular member 22 is inserted into the collection vessel 10 with the end 28 containing the membrane filter 32 immersed in the preservation fluid 12, as shown in FIG. 3. The suction tube 40 is coupled to a vacuum/pressure source (not shown) and the valves 44, 46 are closed. At this point, the vacuum/pressure source is activated and the valve 44 to the suction tube 40 opened so as to create a vacuum inside the interior of the tubular member 22 and a pressure gradient across the membrane filter 32. This causes the preservation fluid 12 to be drawn through the membrane filter 32 and up into the interior of the tubular member 22. As depicted in FIGS. 3 and 4, the membrane filter 32 comprises a series of pores 33 which are smaller than the biological target cells (indicated by reference 100), but larger than the debris, mucus and other contaminants (indicated by reference 102) which may be present and suspended in the preservation fluid 12. As a result, the membrane filter 32 allows the debris, mucus and other contaminants to pass as indicated by arrow A (FIG. 4) while trapping the biological target cells 100.

The next step involves extracting the biological target cells 100. The density and number of biological target cells 100 trapped on the membrane filter 32 is controlled by varying the vacuum inside the tubular member 22. Preferably, the vacuum inside the tubular member 22 is controlled so that the biological target cells 100 are distributed uniformly over the surface of the membrane filter 32. However, debris, mucus and other contaminants 102 contained in the preservation fluid 12 may also become trapped, or "caked" on the membrane filter 32 during the extraction step, together with the biological target cells 100. To minimize the collection of debris 102 on the membrane filter 32, the flow rate of preservation fluid 12 across the membrane filter 32 is kept relatively low by maintaining a low vacuum inside the tubular member 22, to produce a flow rate in the range of 5 to 500 microliters per second.

Figure 5E:
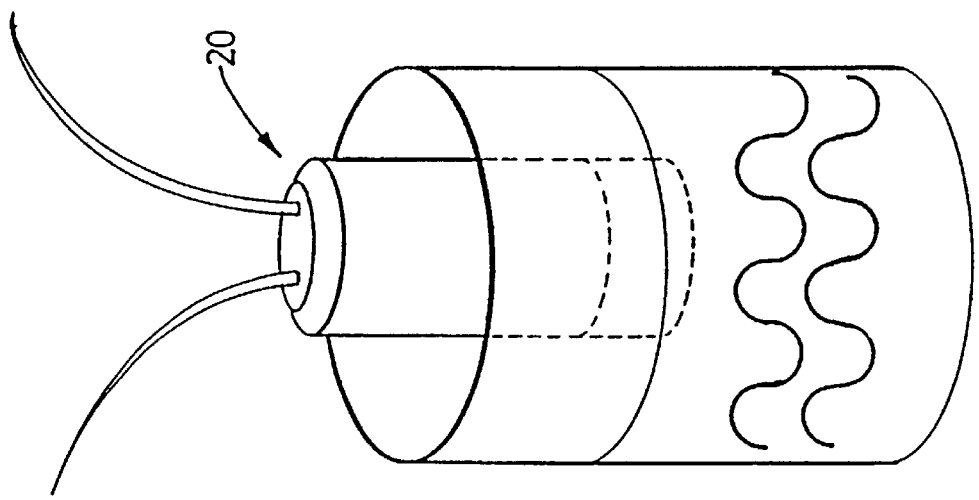
FIG. 5(e) is a schematic view of the filter tube being subjected to sonic agitation during the extraction step.
Figure 5D:
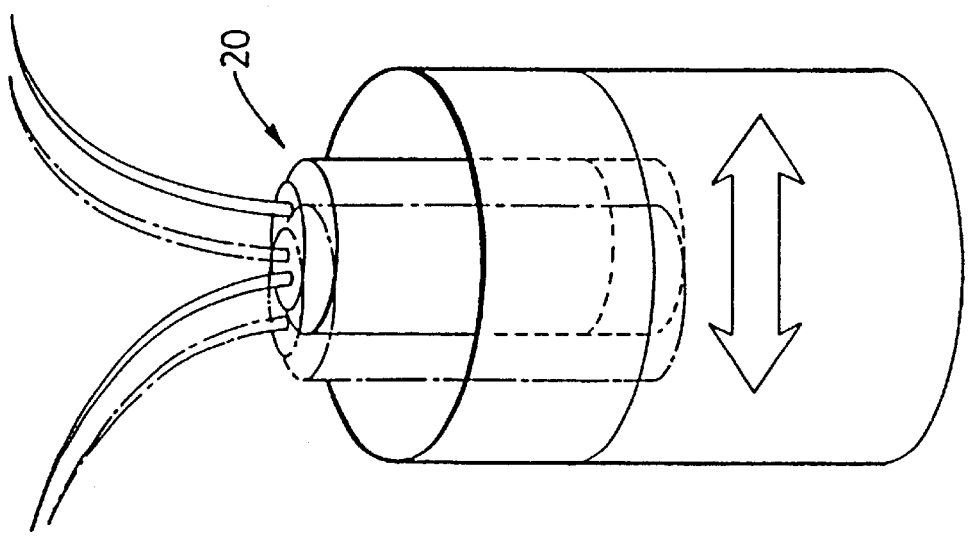
FIG. 5(d) is a schematic view of the filter tube being subjected to mechanical agitation during the extraction step.

Despite the maintenance of a low flow rate of preservation fluid 12 through the membrane 32, it is still possible that some debris 102 will become caked on the membrane filter 32. According to one variation of the extraction step, the tubular member 22 undergoes mechanical or sonic agitation while the preservation fluid 12 is slowly drawn across the membrane filter 32. The mechanical or sonic agitation loosens the trapped debris 102 from the membrane filter 32, thereby allowing the debris 102 to more readily pass through the membrane filter 32. Advantageously, the mechanical or sonic agitation also allows the biological target cells 100 to be more uniformly distributed over the surface of the membrane filter 32. The application of mechanical agitation to the filter tube 20 is depicted in FIG. 5(d), while the application of sonic agitation to the filter tube 20 is depicted in FIG. 5(e).

Although the low flow rate of preservation fluid 12 allows an automated control system to control the density and number of biological target cells 100 accumulated on the membrane filter 32 while minimizing the collection of debris 102 on the membrane filter 32, the low flow rate also increases the duration of the extraction step. In another variation of the extraction step, the flow rate of preservation fluid 12 across the membrane filter 32 is kept relatively high by maintaining a high vacuum inside the tubular member 22 (depicted in FIG. 5(a)). While the high flow rate shortens the duration of the extraction step, it also increases the amount of caking on the membrane filter 32. To reduce the accumulation of debris 102 on the membrane filter 32, the rapid draw of preservation fluid 12 across the membrane filter 32 is momentarily interrupted with a back flushing step (depicted in FIG. 5(b)).

During the back flushing step, the valve 44 to the suction tube 40 is momentarily closed and the valve 46 to the drain/fill tube 42 is momentarily opened. This equalizes the pressure in the tubular member 22 with the atmospheric pressure and allows the preservation fluid 12 in the tubular member 22 to drain out through the membrane filter 32, as indicated by arrows B in FIG. 5(b). Since the direction of flow of the preservation fluid 12 across the membrane filter 32 during the back flushing step is directly opposite to the direction of flow of preservation fluid 12 prior to the back flushing step, the debris 102 and biological target cells 100 trapped on the membrane filter 32 are released from the membrane filter 32 and become substantially uniformly distributed in the preservation fluid 12.

After the "back flushing step", the valve 46 to the drain/fill tube 42 is closed and the valve 44 to the suction tube 40 is re-opened to re-establish the high vacuum inside the tubular member 22 and the high flow rate of preservation fluid 12 across the membrane filter 32 (depicted in FIG. 5c). Since the back flushing step substantially uniformly distributes the biological target cells 100 throughout the preservation fluid 12, the biological target cells 100 become substantially uniformly distributed over the surface of the membrane filter 32 as also depicted in FIG. 5(c).

The draw of the preservation fluid 12 across the membrane filter 32 continues for a fixed period of time until a desired density and number of biological target cells 100 on the membrane filter 32 is reached. At this point, the valve 44 to the suction tube 40 is closed to keep the biological target cells 100 trapped on the membrane filter 32. Alternately, since the resistance to fluid flow across the membrane filter 32 is a function of the density and number of biological target cells 100 trapped on the membrane filter 32, the fluid flow resistance across the membrane filter 32 is continuously monitored. When the fluid flow resistance reaches a threshold level, indicative of the desired density and number of biological target cells 100, further draw of preservation fluid 12 across the membrane filter 32 is terminated by closing the valve 44.

Figure 6:
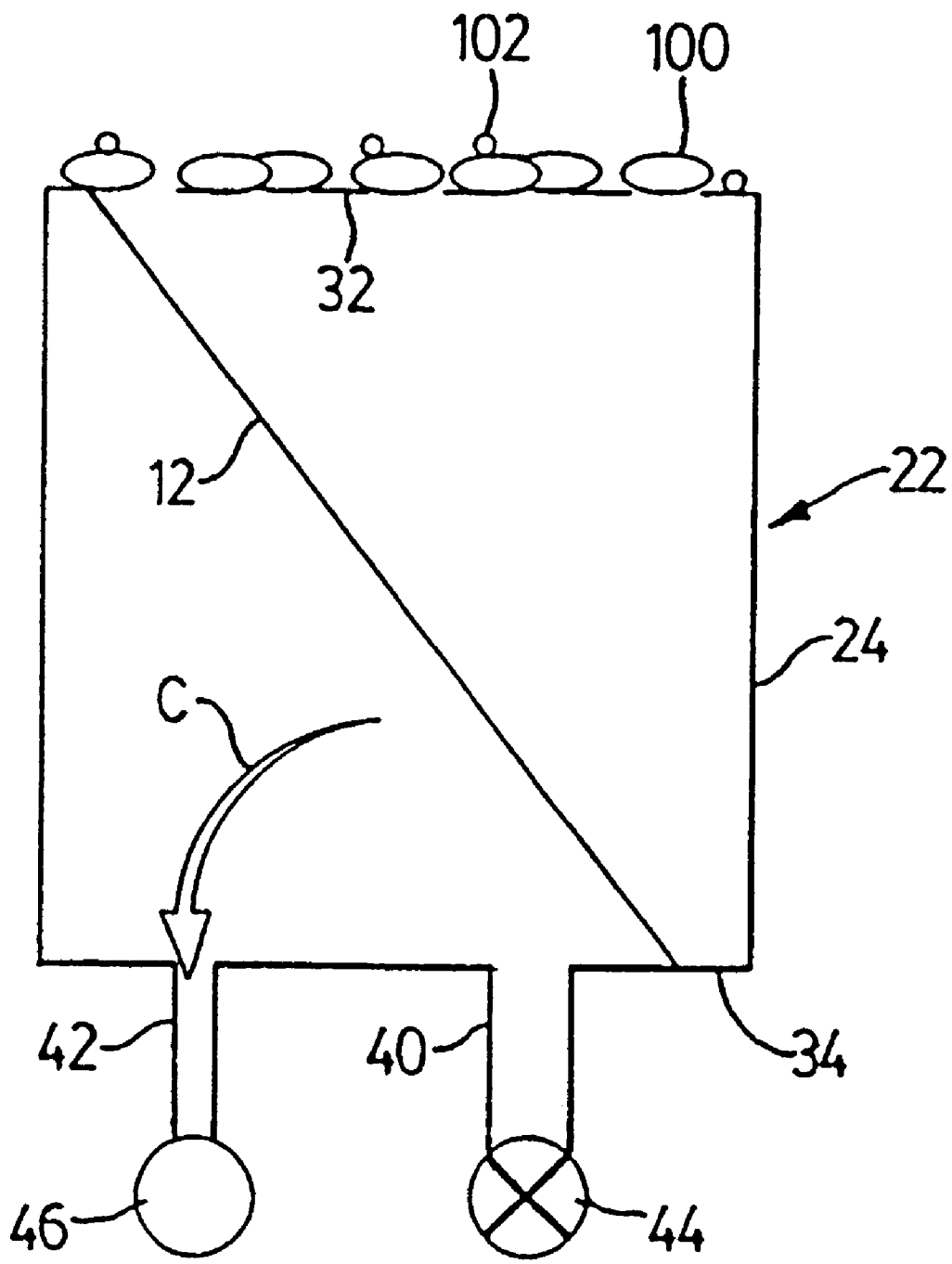
FIG. 6 is a magnified schematic view of the filter tube at the end of the extraction step.

With the biological target cells 100 substantially uniformly distributed over the surface of the membrane filter 32, the extraction step is completed by removing the filter end 28 of the tubular member 22 from the collection vessel 10. The biological target cells are retained on the membrane filter 32 due to the pressure gradient maintained across the membrane filter 32. The tubular member 22 is then inverted, as shown in FIG. 6, and the valve 46 to the drain/fill tube 42 is opened to allow any preservation fluid 12 remaining in the tubular member 22 to drain out the drain/fill tube 42 in the direction of the arrow C. The valve 46 is then closed, and the tubular member 22 inverted in preparation for a biological target cell distribution step.

The biological target cell distribution step comprises bringing the tubular member 22 in close proximity to a substrate 48, as shown in FIG. 7(a). The substrate 48 comprises a microscope slide 50 having an upper substrate surface 52 and a settling chamber 54. The settling chamber 54 is tubular in shape and includes an interior region 56 bounded by an inner cylindrical wall 58, a lower end face 60, and a first resilient O-ring 62 secured to the inner tubular wall 58. A second resilient O-ring 64 is permanently secured to the lower end face 60 and the upper substrate surface 52 so as to provide a leak resistant seal between the lower end face 60 and the upper substrate surface 52.

As shown in FIG. 7(b), the settling chamber 54 receives the tubular member 22 inside the interior region 56. As part of the biological cell distribution step, the tubular member 22 is inserted into the interior region 56 so that the first O-ring 62 seals the outer tubular surface 24 of the tubular member 22 to the settling chamber 54. The tubular member 22 is moved towards the microscope slide 50 until the end 28 of the member 22 is proximate to the upper substrate surface 52.

Figure 8:
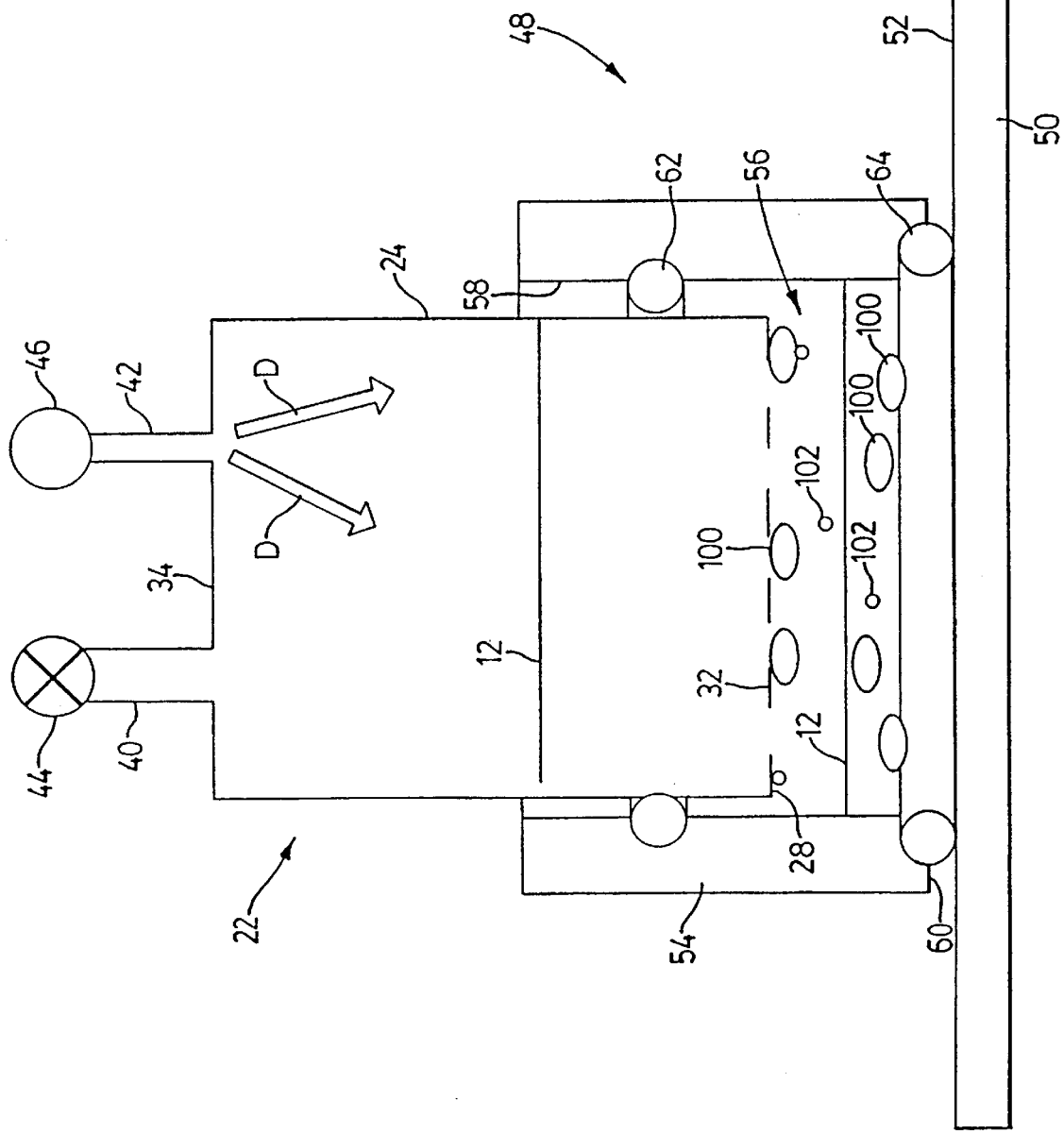
FIG. 8 is a magnified schematic view of the filter tube and substrate during the distribution step.

Next, the valve 46 to the drain/fill tube 42 is opened and fluid., such as the preservation fluid 12, introduced into the interior 24 of the tubular member 22 through the drain/fill tube 42, in the direction of the arrow D as depicted in FIG. 8. The biological target cells 100 are detached, or washed, from the membrane filter 32 and placed in fluid suspension in the interior region 56 between the upper substrate surface 52 and the end 28 of the tubular member 22.

Figure 9:
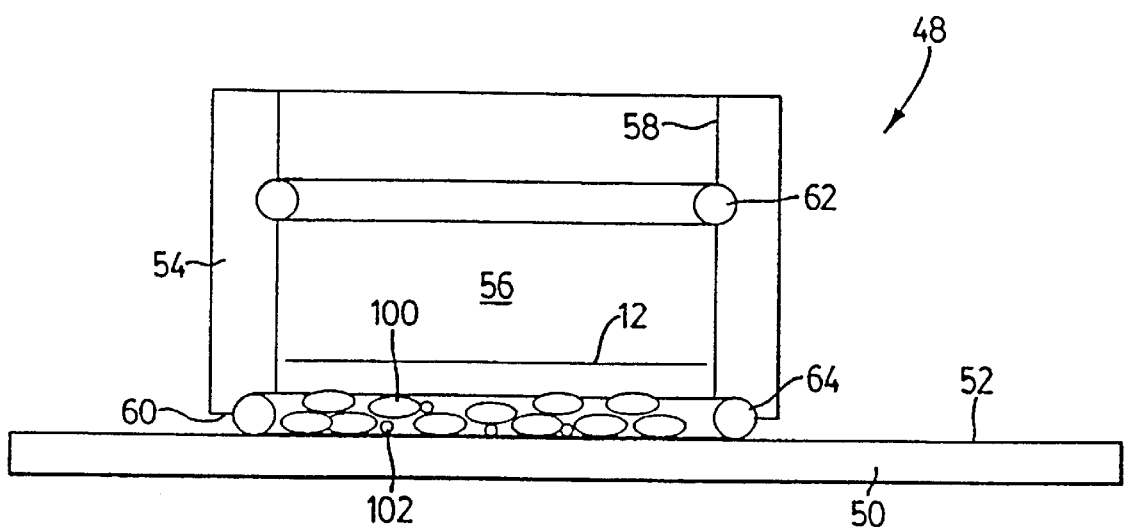
FIG. 9 is a magnified schematic view of the filter tube and substrate at the end of the distribution step.

Referring next to FIG. 9, the biological target cells 100 are allowed to settle onto the upper substrate surface 52 of the slide 52 under the influence of gravity. Since the biological target cells 100 are substantially uniformly distributed over the surface of the membrane filter 32 prior to the distribution step, the biological target cells 100 will also be substantially uniformly distributed over the upper substrate surface 52. To enhance the uniform distribution of the biological target cells 100, the settling chamber 54 is gently agitated during the distribution step in a further variation.

Figure 10B:
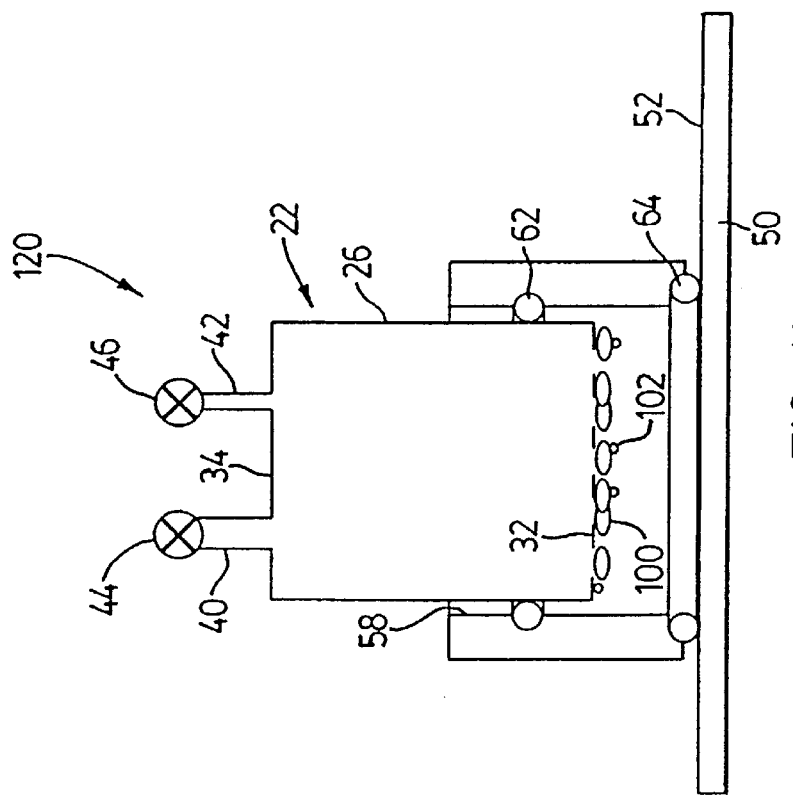
FIGS. 10(a) to 10(b) are magnified schematic views of a variation of the filter tube and substrate shown in FIG. 7.
Figure 10A:
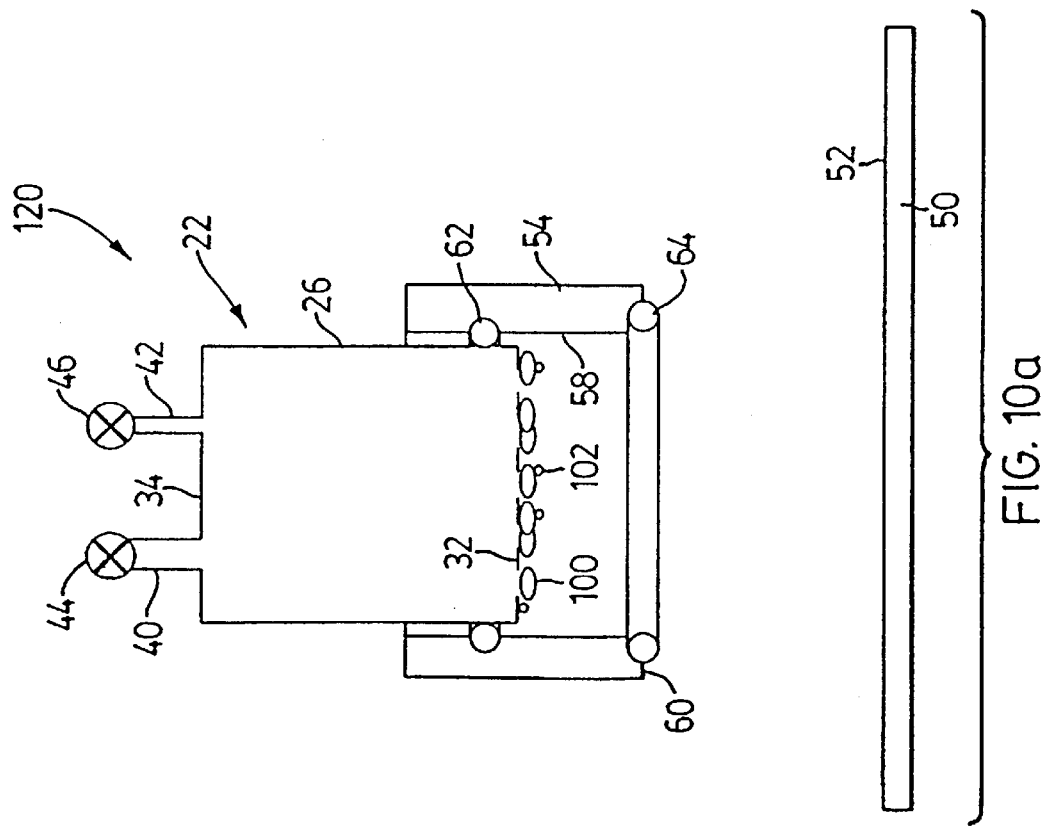
Figure 13:
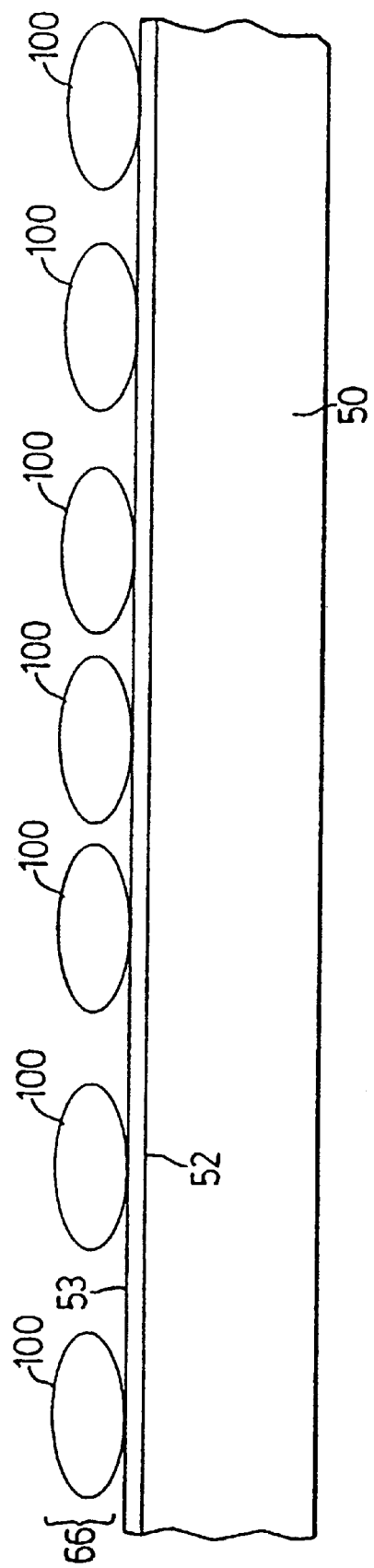
FIG. 13 is a magnified schematic view of the biological target cells and the substrate surface at the end of the removal step.

In another variation of the distribution step, a filter tube denoted by 120 in FIG. 10(a) is used to extract the target biological cells 100 during the extraction step. The filter tube 120 is identical to the filter tube 20 (FIG. 7) except that the first resilient O-ring 62 is permanently secured to the outer tubular surface 26 of the tubular member 22 and the inner tubular wall 58 of the settling chamber 54 so as to provide a leak resistant seal between the tubular member 22 and the settling chamber 54. As shown in FIG. 10(*b*), the second resilient O-ring 64, provided at the lower end face 60 of the settling chamber 54, is pressed against the upper substrate surface 52 of the microscope slide 50 so as to provide a leak resistant seal between the lower end face 60 and the upper substrate surface 52. The biological target cells 100 are then washed onto the upper substrate surface 52 as described above.

As shown in FIG. 11, by the end of the distribution step the biological target cells 100 will be distributed over the upper substrate surface 52 into a primary layer 66 and at least one secondary layer 68. The primary layer 66 is located immediately adjacent the upper substrate surface 52 and the secondary layer 68 located above the primary layer 66 as shown in FIG. 11. Due to the proximity of the primary layer 66 with the upper substrate surface 52, the biological target cells 100 located in the primary layer 66 become attached to the upper substrate surface 52.

Referring to FIG. 12, the next step comprises a cellular removal step. The cellular removal step comprises spraying the biological target cells 100 with a fluid stream 12', such as the preservation fluid, as shown in FIG. 12. Since the biological target cells 100 located in the primary layer 66 form a stronger bond with the upper substrate surface 52 than do the biological target cells 100 located in the secondary layers 68, the biological target cells 100 in the secondary layers 68 will be washed away while the biological target cells 100 in the primary layer 66 will remain attached to the upper substrate surface 52 as shown in FIG. 13.

In one variation of the above cellular removal step, the upper substrate surface 52 is provided with a polymer layer 53 (FIG. 13), such as poly-L-lysine, which improves the strength of attachment between the upper substrate surface 52 and the biological target cells 100 in the primary layer 62. In another variation, the biological target cells 100 in the secondary layers 68 are removed by immersing the substrates 48 in a fluid, such as the preservation fluid 12, and then agitating the substrate 48 in the fluid.

Figure 14:
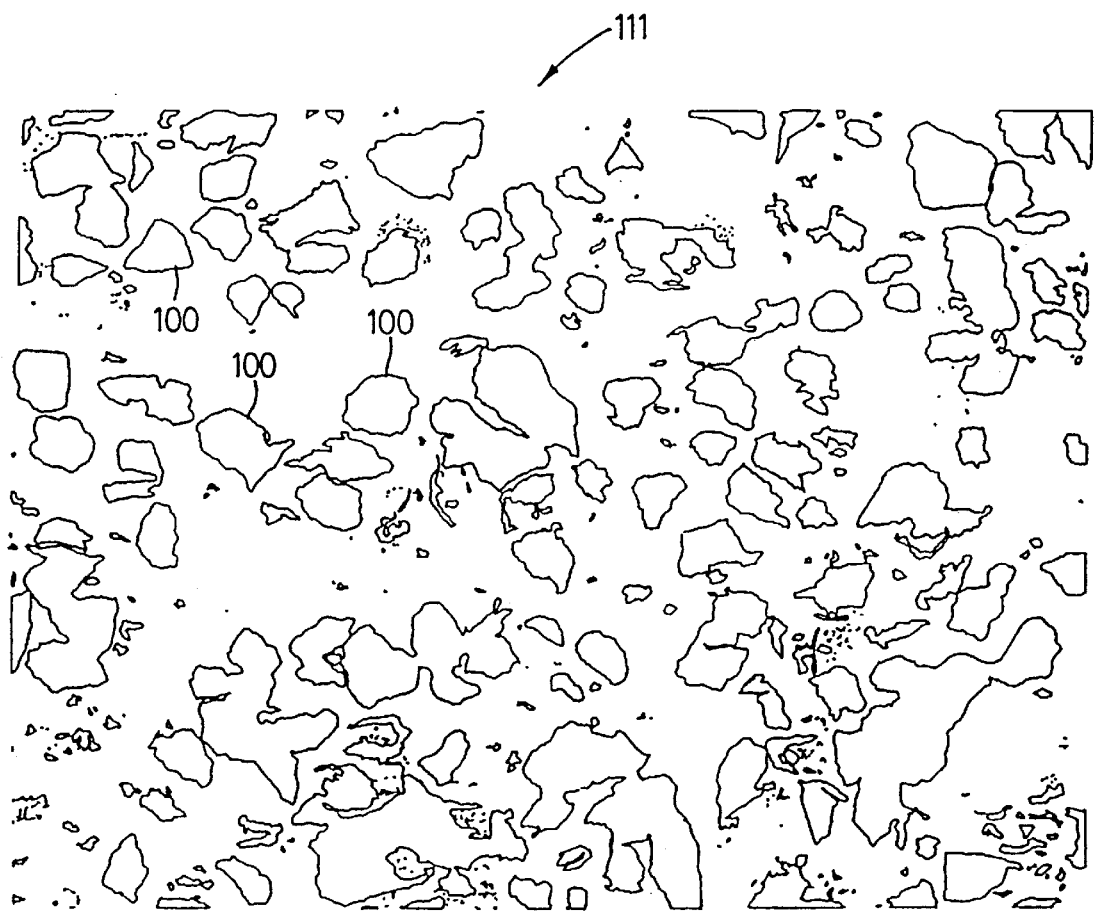
FIG. 14 is a specimen of cervical epithelial cells prepared according to the invention.

Reference is next made to FIG. 14 which shows a cervical epithelial cell specimen 111 prepared according to the described invention, using a microscope slide 50 coated with poly-L-lysine polymer. Advantageously, the specimen 111 comprises a single layer of biological target cells which do not overlap and are ready for subsequent preparation steps, such as staining, cover-slipping etc. For example, the specimen 111 depicted in FIG. 14 represents the distribution and density of cervical epithelial cells taken from the uterine cervix and subjected to the standard Papanicolaou protocol (i.e. PAP test).

Figure 11:
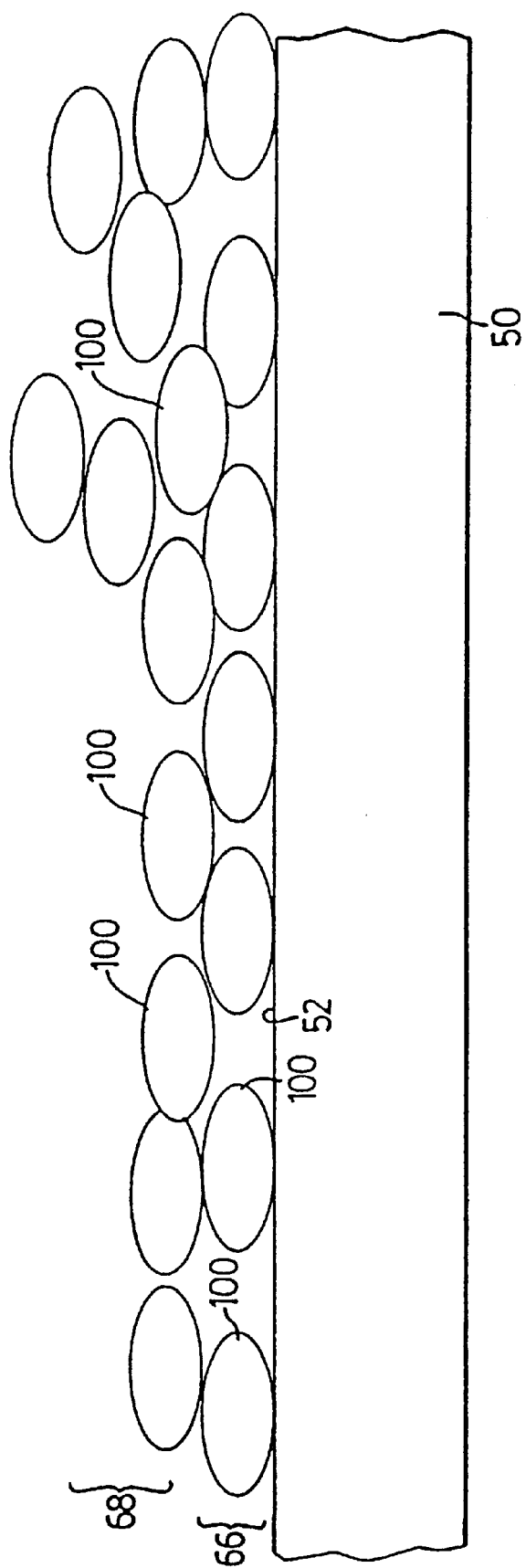
FIG. 11 is a magnified schematic view of the biological target cells at the end of the distribution step, showing the primary and secondary layers.
Figure 12:
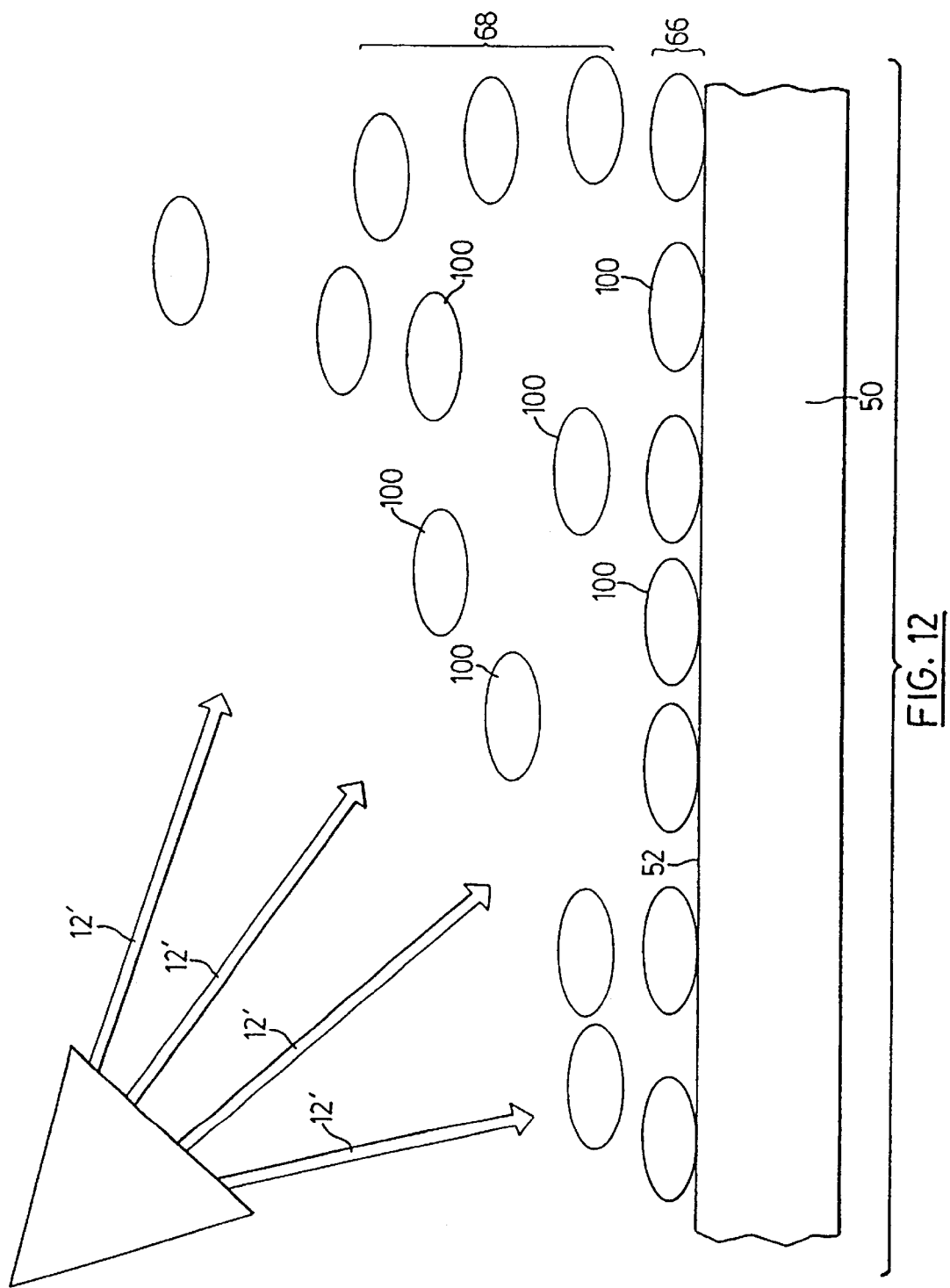
FIG. 12 is a magnified schematic view of the biological target cells during the removal step.
Figure 15:
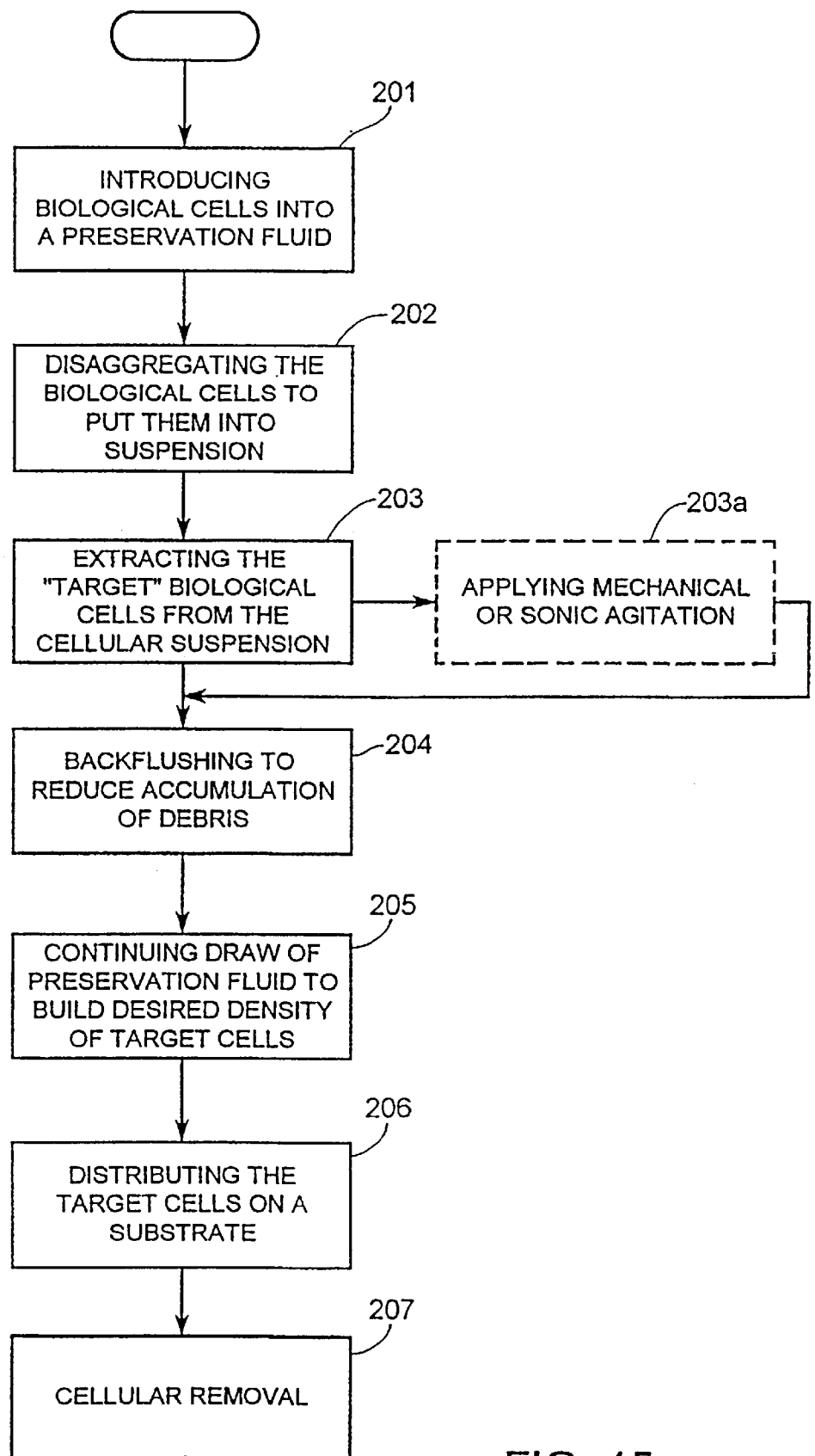
FIG. 15 is a flow chart showing the method steps for preparing a specimen from a cellular suspension according to the present invention.

Reference is next made to FIG. 15 which shows a flow chart summarizing the method steps for preparing a specimen from a cellular suspension according to the present invention. The first step in block 201 comprises introducing the biological cells 10 in a preservation fluid 12 (FIG. 1). The second step in block 202 comprises disaggregating the cells to put them into suspension in the preservation fluid 12. The third step in block 203 involves extracting the target biological cells 100 (FIG. 5) from the suspension of cells. The extraction step 203 may include the application of mechanical or sonic agitation (block 203a shown in broken outline) to reduce "caking" of cells on the membrane filter 32 (FIG. 2). The next step in block 204 involves back flushing to reduce the accumulation of debris on the membrane filter 32. The back flushing step 204 involves momentarily interrupting the draw of preservation fluid through the membrane filter 32. The next step in block 205 involves continuing the draw of preservation fluid 12 through the membrane filter 32 until the desired density and number of target biological cells 100 are accumulated on the membrane filter 32. The next step in block 206 comprises distributing the target biological cells from the membrane filter 32 to a substrate 50 (FIG. 7). The last principle step in block 207 comprises a cellular removal step in which the secondary layer(s) 68 (FIG. 11) of cells 100 on top of the primary layer 66 on the substrate 50 are removed. The cells 100 in the secondary layer 68 are washed away so that the target cells 100 in the primary layer 66 remain attached to the substrate 50.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method of preparing a biological cellular specimen on the surface of a substrate, said method comprising the steps of:
    providing a suspension of biological cells in fluid wherein said cells include biological target cells;
    extracting a portion of the biological target cells from the suspension;
    distributing the extracted portion of said biological target cells over the surface of the substrate into a primary layer with the remaining extracted biological target cells being located above said primary layer; and
    removing the said biological target cells located above said primary layer.

2. The method according to claim 1, wherein said distribution step comprises washing the extracted target cells onto the surface of the substrate, and agitating the target cells.

3. The method according to claim 1, wherein the surface of said substrate includes an adhesive enhancing coating for enhancing adhesion between the primary layer and the surface of said substrate, and wherein said distribution step comprises washing the extracted target cells onto said adhesive enhancing coating.

4. The method according to claim 3, wherein said adhesive enhancing coating comprises poly-L-lysine polymer.

5. The method according to claim 1, wherein said step of providing a suspension comprises depositing said biological cells in the fluid, and agitating said fluid to break apart clusters of said biological cells.

6. The method according to claim 5, wherein said step of agitating comprises vortex agitation.

7. The method according to claim 1, wherein said extraction step comprises passing said cellular suspension in a filtering direction through a filter, and removing debris and contaminant build-up on said filter.

8. The method according to claim 7, wherein said step of removing debris comprises agitating the filter.

9. The method according to claim 8, wherein said step of agitating comprises mechanical agitation.

10. The method according to claim 8, wherein said step of agitating comprises sonic agitation.

11. The method according to claim 7, wherein said step of removing debris comprises passing fluid through the filter in a direction opposite to the filtering direction.

12. The method according to claim 1, wherein said step of extracting comprises filtering the cellular suspension through a filter having pores smaller than the target cells, and trapping the target cells on the filter.

13. The method according to claim 12, wherein said step of trapping comprises maintaining a pressure gradient across the filter.

14. The method according to claim 1, wherein said step of removing comprises spraying the distributed cells with a fluid.

15. The method according to claim 1, wherein step of removing comprises immersing the substrate in a fluid, and agitating the substrate in the fluid.

* * * * *